(12) United States Patent
Sun et al.

(10) Patent No.: US 9,012,365 B2
(45) Date of Patent: Apr. 21, 2015

(54) COMPATIBILITY AGENTS FOR HERBICIDAL FORMULATIONS COMPRISING 2,4-(DICHLOROPHENOXY) ACETIC ACID SALTS

(75) Inventors: Jinxia Susan Sun, Hopewell, NY (US); Shawn Zhu, Stormville, NY (US); Shuaib A. Khan, Danbury, CT (US)

(73) Assignee: Akzo Nobel N.V., Arnhem (NL)

( * ) Notice: Subject to any disclaimer, the term of this patent is extended or adjusted under 35 U.S.C. 154(b) by 701 days.

(21) Appl. No.: 12/518,029

(22) PCT Filed: Mar. 30, 2007

(86) PCT No.: PCT/US2007/008230
§ 371 (c)(1),
(2), (4) Date: Jul. 8, 2009

(87) PCT Pub. No.: WO2008/069826
PCT Pub. Date: Jun. 12, 2008

(65) Prior Publication Data
US 2009/0305896 A1 Dec. 10, 2009

Related U.S. Application Data

(60) Provisional application No. 60/873,158, filed on Dec. 6, 2006.

(51) Int. Cl.
| | | |
|---|---|---|
| A01N 39/02 | (2006.01) | |
| A01N 25/30 | (2006.01) | |
| A01N 39/04 | (2006.01) | |
| C05G 3/02 | (2006.01) | |
| A01N 33/02 | (2006.01) | |
| A01N 43/40 | (2006.01) | |
| A01N 43/60 | (2006.01) | |
| A01N 43/76 | (2006.01) | |
| A01N 43/78 | (2006.01) | |
| A01N 33/12 | (2006.01) | |

(52) U.S. Cl.
CPC ............... *A01N 39/02* (2013.01); *A01N 25/30* (2013.01); *A01N 39/04* (2013.01); *C05G 3/02* (2013.01)

(58) Field of Classification Search
USPC ............... 504/189, 194, 195, 209, 321, 322; 564/280, 281, 291, 294, 295
See application file for complete search history.

(56) References Cited

U.S. PATENT DOCUMENTS

| | | | |
|---|---|---|---|
| 3,276,856 A | 10/1966 | Esposito | |
| 5,658,855 A | 8/1997 | Nalewaja et al. | |
| 5,877,112 A * | 3/1999 | Roberts et al. | 504/206 |
| 6,130,186 A * | 10/2000 | Ward et al. | 504/365 |
| 6,645,914 B1 | 11/2003 | Woznica et al. | |
| 7,060,659 B2 | 6/2006 | Killick et al. | |
| 2001/0029240 A1 * | 10/2001 | Hasebe et al. | 504/334 |
| 2002/0160916 A1 * | 10/2002 | Volgas et al. | 504/194 |
| 2003/0153462 A1 | 8/2003 | Herold et al. | |
| 2004/0038826 A1 * | 2/2004 | Kurita et al. | 504/127 |
| 2005/0215434 A1 | 9/2005 | Ruiz et al. | |
| 2006/0019828 A1 * | 1/2006 | Becher et al. | 504/116.1 |
| 2010/0056375 A1 | 3/2010 | Jönsson et al. | |

FOREIGN PATENT DOCUMENTS

| | | | | |
|---|---|---|---|---|
| AU | 2004100006 A4 | 3/2004 | | |
| DE | 2 327 189 | 12/1974 | | |
| DE | 30 02 053 A1 | 8/1980 | | |
| DE | 3002053 A1 | 8/1980 | | |
| DE | 3337044 A1 * | 4/1983 | ............ | C07D 215/16 |
| EP | 0 257 686 A1 | 3/1988 | | |
| EP | 0257686 A1 * | 3/1988 | ............. | A01N 25/30 |
| EP | 0 299 654 A2 | 6/1988 | | |
| EP | 0 360 181 A1 | 3/1990 | | |
| GB | 1 339 315 | 12/1973 | | |
| GB | 2 233 229 A | 1/1991 | | |
| WO | WO 81/01787 | 7/1981 | | |
| WO | WO 00/30452 | 6/2000 | | |
| WO | WO 00/64257 | 11/2000 | | |
| WO | WO 00/64258 | 11/2000 | | |
| WO | WO 01/32019 A1 | 5/2001 | | |
| WO | WO 01/89302 A2 | 11/2001 | | |
| WO | WO 01/95720 A1 | 12/2001 | | |
| WO | WO 02/32227 A1 | 4/2002 | | |
| WO | WO 02/063955 A2 | 8/2002 | | |
| WO | WO 02/078442 A2 | 10/2002 | | |
| WO | WO 02/096199 A2 | 12/2002 | | |
| WO | WO 02/102153 A2 | 12/2002 | | |
| WO | WO 03/026422 A1 | 4/2003 | | |
| WO | WO 2004/093546 A1 | 11/2004 | | |

(Continued)

OTHER PUBLICATIONS de Ruiter et al., "Influence of Two Fatty Amine Surfactants on Foliar Absorption, Translocation, and Efficacy of 2,4-D Triethanolamine Salt," 1995, J. Agric. Food Chem., 43:3093-3097.*
Inorganic bases, Sigma-Aldrich [online], [retrieved Jun. 16, 2014] Retrieved from the Internet: URL:http://www.sigmaaldrich.com/chemistry/chemistry-products.html?TablePage=16281251.*
European Search Report for International Application No. 07010792.5; Completion Date: Oct. 9, 2007.
International Search Report for International Application No. PCT/EP2007/063129; Completion Date: Sep. 5, 2008.
De Ruiter, H.: "2, 4-D salts and adjuvants review and perspectives"; vol. 23; pp. 95-105 (2003) (XP009090474).
Derwent Abstract No. 90-092788/13 of European Publication No. 360181A, (1989).
L.L. Jansen; "Herbicidal and Surfactant Properties of Long-chain Alkylamine Salts of 2,4-D in Water and Oil Sprays," Weeds; pp. 123-130 (1965).

(Continued)

*Primary Examiner* — Jane C Oswecki
(74) *Attorney, Agent, or Firm* — Norris McLaughlin & Marcus, P.A.

(57) ABSTRACT

The present invention generally relates to a method for minimizing the formation of insoluble salts of phenoxy herbicides. The method comprises (1) mixing a compatibility agent, amine salts of phenoxy acid herbicides, and a chemical containing non-amine cations in a aqueous system to form a stable and non-nozzle plugging solution; and (2) application of said stable and non-nozzle plugging solution onto target plants.

40 Claims, 3 Drawing Sheets

(56) References Cited

FOREIGN PATENT DOCUMENTS

| WO | WO 2005/087007 A1 | 9/2005 | |
|---|---|---|---|
| WO | WO2005/087007 A1 * | 9/2005 | ............ A01N 57/20 |

OTHER PUBLICATIONS

International Search Report for International Application No. PCT/US2007/008230; Completion Date: Oct. 23, 2007.

De Ruiter, H.: "Influence of two fatty amine surfactants on Foliar Absorption, and Efficacy of 2,4-D Triethanolamine Salt,"J. Agric. Food Chem., vol. 43, pp. 3093-3097(1995).

XP-002456048; CAPLUS Abstract; Sharma et al., "Foliar penetration of picloram and 2,4-D in aspen and . . . ," J. of Plant Growth Regulations, vol. 4, No. 4, pp. 189-201 (1986).

XP-002456049; CAPLUS Abstract; Morre et al., "Mefluidide-chlorsulfuron-2,4-D surfactant combinations for roadside . . . ," Weed Science, vol. 18, No. 1, pp. 57-63 (1970).

Derwent Abstract No. 0000592267 of German Publication No. 2327189A, (1974).

Abstract of German Publication No. 3002053A1, (1980).

Derwent Abstract No. 0000592267 of German Publication No. 2327189A (2009).

Abstract of German Publication No. 3002053A1 (2009).

European Search Report for International Application No. 07010792.5; Completion Date Oct. 9, 2007.

International Search Report for International Application No. PCT/EP2007/063129; Completion Date Sep. 5, 2008.

De Ruiter, H.: "2, 4-D salts and adjuvants review and perspectives"; vol. 23, pp. 95-105 (2003) (XP009090474).

Derwent Abstract No. 90 092788/13 of European Publication No. 360181A, (1989).

* cited by examiner

COMPATIBILITY AGENTS FOR HERBICIDAL FORMULATIONS COMPRISING 2,4-(DICHLOROPHENOXY) ACETIC ACID SALTS

FIELD OF THE INVENTION

The present invention generally relates to a method for minimizing the formation of insoluble salts of phenoxy herbicides. The method comprises (1) mixing a compatibility agent, amine salts of phenoxy acid herbicides, and a chemical containing non-amine cations in an aqueous system to form a stable and non-nozzle plugging solution; and (2) the method of applying the stable and non-nozzle plugging solution onto a plant.

BACKGROUND OF THE INVENTION

Phenoxy herbicides, especially 2,4-D, is well known in the art as an effective herbicide for the control broad leaf weeds. From this point on, we will use 2,4-D as the example but those skilled in the an should realize that although 2,4-D is mentioned it should be understood that it also applies generally to the entire phenoxy herbicide family.

It is a common practice for farmers to add 2,4-D amine herbicide to a concentrated liquid fertilizer (such a 28% N) and to spray it without further dilution with water. 2,4-D amine herbicide is also widely used together with other herbicides and diluted fertilizers such as ammonium sulfate (AMS) to enhance the bioefficacy and to achieve a broader weed control spectrum. However, 2,4-D acid and its non-amine salts have very low solubility in water. Because of this, the most commonly used 2,4-D herbicide is 2,4-D amine salts. Although hydrophobic 2,4-D esters are available, 2,4-D formulated and applied as a water-soluble salt has the added advantages of not requiring an emulsifier and/or an organic solvent.

It is a common practice for farmers to mix various products in a spray tank for convenience and economy reasons. For example, farmers may mix together a 2,4-D product and a fertilizer product. However, when a 2,4-D amine product is mixed with another product that contains non-amine cations, such as ammonium, sodium, potassium, and multivalent ions, a precipitate can form in the spray tank resulting in the blockage of the spray nozzle. Even if farmers intentionally try to avoid mixing 2,4-D with incompatible components, it may not be possible to avoid having both 2,4-D anion and non-amine cations in the same spray tank because ammonium, K, Na, Ca, and Mg may come from, for example, fertilizers, other herbicide formulations, micronutrients, or hard water, thereby causing unwanted precipitate. Farmers have been trying to solve this precipitate problem by adding traditional compatibility agents or hydrotropes such as phosphate esters, glycols, or alcohol without satisfactory result.

Accordingly, it is desirable to develop a method for minimizing the formation of nozzle plugging precipitate in a vessel containing a 2,4-D herbicide and non-amine cations.

It is, therefore, an objective of the present invention to provide a method for minimizing the formation of nozzle plugging precipitate in a vessel containing a 2,4-D herbicide and non-amine cations by using a suitable compatibility agent. It is a further and preferred objective to provide a method of using a surfactant which not only functions as a compatibility agent for precipitation crystal-free spray application but also as an adjuvant for improved efficacy.

SUMMARY OF THE INVENTION

The present invention relates to herbicide formulations free from nozzle plugging particles comprising 2,4-D anion and a compatibility agent in the presence of non-amine cations and a method to minimize the formation of nozzle plugging particles in such a system.

BRIEF DESCRIPTION OF THE DRAWINGS

The invention will now be described with reference to the drawings, wherein.

DETAILED DESCRIPTION OF THE INVENTION

Some chemicals have been found to apparently improve the solubility of another in water. Such a chemical is sometimes called a hydrotrope and it is defined as the ability of some agents to increase the solvent power of water towards other molecules. The phenomenon refers mainly to the increased solubility of ethoxylated products in water due to the addition of a hydrotrope. The other phenomenon of hydrotropy, commonly employed in shampoo and cleaner formulations, refers to the reduced viscosity of the product by using hydrotropes to prevent a liquid crystalline formation in the micellar system. This effect of hydrotropy differs from the solubilization properties of surfactants which results in a third hydrophobic material being enclosed in a microstructure such as micelle or microemulsion, the whole thing being dispersed in water. The chemical which increases the solubility of a hydrophobic material is called a solubilizer or coupling agent and it is generally referred to as a surfactant.

Many chemicals have been called fertilizer compatibility agents. Examples of common fertilizer compatibility agents include phosphate esters, alkylpolyglycosides, nonionic nonylphenol ethoxylates, and the like. Specifically, they prevent the diluted pesticide emulsion from separating out in the presence of fertilizer and another herbicide.

It is an objective of the present invention to increase the aqueous solubility of non-amine salts of phenoxy acid herbicides. Examples of phenoxy acid herbicides referred to in the present invention include, but are not limited to the following.

phenoxyacetic herbicides
    4-CPA
    2,4-D
    3,4-DA
    MCPA
    MCPA-thioethyl
phenoxybutyric herbicides
    4-CPB
    2,4-DB
    3,4-DB
    MCPB phenoxypropionic herbicides
    cloprop
    4-CPP
    dichlorprop
        dichlorprop-P
    3,4-DP
    fenoprop
    mecoprop
        mecoprop-P
aryloxyphenoxypropionic herbicides
    chlorazifop
    clodinafop
    clofop
    cyhalofop
    diclofop
    fenoxaprop
        fenoxaprop-P
    fenthiaprop
    fluazifop
        fluazifop-P
    haloxyfop
        haloxyfop-P
    isoxapyrifop
    metamifop
    propaquizafop
    quizalofop
        quizalofop-P
    trifop Although it is believed that the present invention is useful for all of the phenoxy herbicides known to the skilled artisan, including those mentioned above, the present inventors will focus this description on 2,4 D acid and its salts because it is by far the phenoxy herbicide having the widest application and use.

Increasing the solubility of the 2,4-D non-amine salts differs from increasing the solubility of an ethoxylated product through a hydrotropy effect. It also differs from increasing the solubility of an oily product through a solubilization effect. The reason is that a 2,4-D non-amine salt is a salt and is neither an ethoxylated chemical nor an oily, hydrophobic chemical. Additionally, because of its nature, it is not possible to predict which chemical would be useful for increasing the solubility of 2,4-D non-amine salts based on conventional knowledge. In fact, some of the observations made by the present inventors were totally against conventional wisdom. More specifically, the present inventors found that the so called well known "hydrotropes" and "compatibility agents", which may be good for other applications, were not suitable for increasing the solubility of 2,4-D non-amino salt. In this regard, phosphate esters, short chain alkyl glycosides, glycols, nonylphenol ethoxylate, isopropyl alcohol, octanol, sodium xylene sulfonate, ethoxylated (2EO) cocoamide oxides, sodium dioctyl sulfosuccinate, butyl cellosolve acetate, amphoteric surfactants, and methyl 2-pyrrolidinone were found to be ineffective.

In accordance with the present invention it is highly desirable to increase the compatibility between a 2,4-D product and another product containing non-amine cations such as co-herbicides, fertilizers, micronutrients, hard water and the like. In this respect, it has been found that only certain chemicals were effective as the compatibility agents to minimize a precipitate formation in the spray tank when a 2,4-D product is mixed with a non-amine cation containing product. The non-limiting examples of such chemicals are: quaternary amines, alkoxylated (quaternary) amines, amidoamines, ethoxylated esteramines, alkyl alcohol alkoxylates, ethoxylated sorbitans and sorbitol esters, tristyrylphenol ethoxylates, EO-PO block and random copolymers, alkyl olefin sulfonates, carboxylated nonionic alcohols, alkylamide ethoxylates, alkylethersulfate amine salts, sodium alkylnaphthalene sulfonates (formaldehyde polymer) and combinations thereof.

The alkoxylated quaternary surfactants usefully employed in the context of the present invention can be represented by the following general formula:

wherein R1 is a straight or branched chain, saturated or unsaturated alkyl group having from 8 to 22 carbon atoms; R2 is a straight or branched chain, saturated or unsaturated alkyl group having from 1 to 4 carbon atoms; and A is $C_iH_{2i}$ where i is 2 to 4; B is $C_jH_{2j}$ where j is 2 to 6; and $X^-$ is a compatible anion such as methyl sulfate or chloride, f is zero to 10; m and n is an integer of from 1-30 with the proviso that m+n is at least 2, p is 1 to 7 and g can be any number from zero to 6 for each p and independent of p, and q is 1 to 7 with a provision that p may be greater than q. In one embodiment, the A is $C_2H_4$, f=0, and g=0. In another embodiment, the A is $C_2H_4$, f=0, g 0, m+n is 2 to 20, R2 is methyl group, p=1, and X is chloride.

The alkyl quaternary surfactants useful in the invention are represented by the formula:

wherein R1 is a straight or branched chain, saturated or unsaturated alkyl group having from 8 to 22 carbon atoms. R2, R3, and R4 is independently a straight or branched chain, saturated or unsaturated alkyl group having from 1 to 4 carbon atoms. A is $C_iH_{2i}$ where i is 2 to 4; B is $C_jH_{2j}$ where j is 2 to 6; and $X^-$ is a compatible anion such as methyl sulfate or chloride. f is zero to 10; p is 1 to 7 and g can be any number from zero to 6 for each p and independent of p, and q is 1 to 7 with a provision that p may be greater than q. In one embodiment, the A is $C_2H_4$, f=0, and g=0. In another embodiment, the A is $C_2H_4$, f=0, g=0, R2 is methyl group, R3 is a methyl group, R4 is a methyl group, p=1, and X is chloride.

The following alkoxylated amines are useful:

wherein R1 is a straight or branched chain, saturated or unsaturated alkyl group having from 8 to 22 carbon atoms; A is $C_iH_{2i}$ where i is 2 to 4; and B is $C_jH_{2j}$ where j is 2 to 6. f is zero to 10; m and n is an integer of from 0-30 with the proviso that m+n is at least 1, p is 1 to 7 and g can be any number from zero to 6 for each p and independent of p. In one embodiment, A is $C_2H_4$, f=0, and g=0. In another embodiment, the A is $C_2H_4$, f=0, g=0, m+n is 1 to 20, p=1.

The following alkoxylated amidoamines are useful:

IV wherein R1 is a straight or branched chain, saturated or unsaturated alkyl group having from 7 to 21 carbon atoms; A is $C_iH_{2i}$ where i is 2 to 4; m is 1 to 30, and n is 1 to 30. The particularly useful R1 is from tall oil, coconut oil, soya oil, corn, or tallow.

The following amidoamines are useful:

V where R1 a straight or branched chain, saturated or unsaturated alkyl group having from 7 to 21 carbon atoms.

The reaction products of fatty acid with polyamines followed by alkoxylation, alkoxylated amido polyamines, are useful. Example of a preferred reaction product has the following structure,

VI wherein R1 is a straight or branched chain, saturated or unsaturated alkyl group having from 7 to 21 carbon atoms; A is $C_iH_{2i}$ where i is 2 to 4; n, m, p, and q all is 1 to 20 independently; x and y is 0 to 5 independently with a provision of x+y greater than or equal to 1. The particularly useful R1 is from tall oil, coconut oil, soya oil, corn, or tallow.

The reaction products of fatty acid and triethanolamine and its alkoxylated products are useful. The preferred species is the monoester which can be represented by the following structure,

VII wherein R1 is a straight or branched chain, saturated or unsaturated alkylene group having from 8 to 22 carbon atoms; A is $C_iH_{2i}$ where i is 2 to 4; m is 1 to 30, and n is 1 to 30.

The following alkyl alcohol alkoxylates are useful,

VIII wherein R1 is a straight or branched chain, saturated or unsaturated alkyl group having from 6 to 14 carbon atoms; A is $C_iH_{2i}$ where i is 2 to 4; and v is 2 to 10 when R1 is linear and 9-20 when R1 is branched.

The following polyethylene sorbitans are useful:

IX where R is C8 to C22, n+m+w is about 10 to 30, preferably 20.

The tristyrylphenol ethoxylate with 8-30 moles of ethylene oxide and its phosphate or salts thereof are useful.

The following EO/PO block and random copolymers are useful,

X wherein R1 is H, or C4 to C10 linear or branched alkyl, A' is C2 or C3, x is 30 to 300, EO:PO>40:60 (weight ratio). When R1=H, they are preferably EO-PO-EO copolymer with a molecular weight >~4000. When R1 is C4 to C10, their molecular weight is preferably >~1500.

The alkyl olefin sulfonate useful in the claimed invention includes alkyl chain length between C8 and C18 and preferably C8-12 olefin sulfonate and salts thereof.

The carboxylated alkylphenol ethoxylate is useful. Preferably it is a carboxylated octylphenol or nonylphenol with 5 to 15 EO. A non-limiting example is the reaction product of nonylphenol ethoxylate (9EO) and sodium monochloroacetate.

Castor oil EO-PO alkoxylate (total 25 to 50 EO+PO units) can also be usefully employed in the context of the present invention.

C8-16 linear or branched alkyl polyglycoside with 1-5, preferably 1-2, glucose units are also useful.

Alkylethersulfate amine salts are useful, and the alkyl chain length is preferably C6 to C12 with 1 to 5 EO groups. The preferred amine is dimethylamidopropylamine (DMAPA), triethanol amine (TEA), diethanolamine (DEA), monoethanolamine (MEA), butylamine, cocoamine, diethylene triamine (DETA), and isopropylamine.

The useful alkylnaphthalene sulfonate (formaldehyde polymer) salt has an alkyl group C8-C18 and the C8-C12 sodium salt is preferred.

Polyethylene sorbitol tallate of the following formula are also useful:

where R is H or a group with the structure:

here R1 is a straight or branched chain, saturated or unsaturated alkyl group having from 7 to 21 carbon atoms; n, m, p, q, x and y is 0 to 20 independently with a provision of n+m+p+q+x+y greater than or equal to 6.

The short amines with the following structure are also useful but they are not the preferred because they are not surfactants and they do not provide other benefits to the herbicides.

Where R1, R2, R3, R4, R5 and R6 are each independently a straight or branched alkenyl group with 1 to 6 carbon atoms; a, b, c, d, e, f, and g are each independently a number from 0 to 40; p is 1-7 independent of a, b, c, d, e, f, and g.

Inorganic bases, such as hydroxides of sodium, potassium, and ammonium can also be used but they are not the preferred because they are not surfactants and they do not provide other benefits to the herbicides. It should also be noted that if glyphosate is present in the herbicidal formulations, the inorganic base is excluded.

As is well known to those skilled in the art, efficacy of many herbicides including 2,4-D is strongly related to the system pH. Typically low pH favors good efficacy. Therefore, it shall be pointed out that using inorganic hydroxides or the short amines, depending on the degree of substitution or its equivalent to minimize the 2,4-D precipitate formation, the system pH could be raised to a value too high to give satisfactory efficacy.

Specific examples of compatibility agents employable in the context of the present invention include, but are not limited to cocoamine-2EO oxide, sodium lauryl sulfate, ethoxylated (6EO), caprylic & capric glycerol ester, C8-10 glycosides, 2-ethylhexyl glycoside, C9-C11 glycoside, iso C13+ 4EO phosphate ester (acid), propyl glycosides, isopropyl alcohol, C8-10+4 EO phosphate ester (acid), alkyl ether citrate, sodium xylene sulfonate, phenol ethoxylate 2-propylheptanol-5EO, sodium dodecylbenzene sulfonate, to butyl cellosolve acetate (C4-O—C—C—OOCC), hexylglycosides, 2-ethylhexanol+35PO+32EO, Na cocoamphocarboxy glycinate, oleylamphopolycarboxyglycinate, EO-PO-EO Block copolymer (40% EO) MW 2900, castor oil ethoxylate-20EO, octyliminodipropionate, EO-PO-EO block copolymer MW 3200, triethyl ammonium phosphate, EO-PO-EO block copolymer (30% EO) MW 1850, EO-PO-EO Block is copolymer (50% EO) MW 1900, methyl-2-pyrrolidinone, EO-PO-EO Block copolymer (40% EO) MW 2200, nonylphenol-12EO, 2-propylheptanol-8EO, trideceth-8, trideceth-6, nonylphenol-9EO, castor oil ethoxylate-55EO, soya acid ethoxylate-10EO, nonylphenol-30EO, C10-12 alcohol ethoxylate (9EO), EO-PO-EO block copolymer (40% EO) MW 5900, C6-10 isopropylamine alcohol ether sulfate, trideceth-10, trideceth-12, sodium alkylnaphthalene sulfonate, formaldehyde polymer, C10-12 alcohol ethoxylate (12EO), polyoxyethylene sorbitol tallate, Di (propylene glycol) methyl ether, lauryldimethyl betaine, cocamide DEA, bottom amines, EO-PO-EO Block copolymer (70% EO) MW 12600, C11 alcohol ethoxylate (5EO), C10-12 alcohol ethoxylate (7EO), EO-PO-EO Block copolymer (70% EO) MW 6600, C10-12 alcohol ethoxylate (7EO), EO-PO-EO Block copolymer (80% EO) MW 13000, EO-PO-EO Block copolymer (80% EO) MW 8400, C8-10 glycosides C10-12 alcohol ethoxylate (SEQ), ethoxylated (20EO) sorbitol ester, 2-Ethylhexanol+13PO+20EO, tristyrylphenol+16EO, EO-PO-EO Block copolymer (50% EO) MW 6500, tallowamine-14EO, tallowamine-2EO, Nonylphenol-9EO carboxylate, C4 with average of 52EO and 46PO, cocoamine-10-EO, cocoamine-5EO, tallowamine-6EO, cocodimethylamidopropylamine, tallowamine-10EO, sodium lauryl olefin sulfonate, tall oil fatty acid amidoamine-10EO, castor oil ethoxylate-36EO, tallowamine-15EO methylchloride, Iso C13 etheramine-5EO, EO-PO-EO Block copolymer (50% EO) MW 4600, sodium lauryl olefin sulfonate, cocotrimethyl chloride, tallow acid+triethanolamine+10EO, cocoamine-2EO, tristyrylphenol+15EO, cocoamine-2EO methylchloride, C4 with average of 61EO and 55PO, coco duoamine-3EO, and mixtures and combinations thereof.

In the herbicidal formulations of the invention, the ratio of said amine salt of a phenoxy acid herbicide, and said compatibility agent is generally between 20:1 to 1:2; in another embodiment, between 10:1 to 1:1.5; and in yet another embodiment 5:1 to 1:1. The concentration of amine salt of the phenoxy acid herbicide is generally between 0.1 to 40% by weight ai based on the weight of the formulation, in another embodiment 1 to 30% by weight and in still another embodiment 2 to 20% by weight.

In one embodiment of the invention, the phenoxy acid herbicide is 2,4-D, and the ratio of 2,4-D amine salt to the compatability agent is between 10:1 to 1:1.5; in another embodiment 5:1 to 1:1. The concentration of 2,4-D amine salt in such formulations is generally between 0.1 to 40% by weight ai based on the weight of the formulation, in another embodiment 1 to 30% by weight and in still another embodiment 2 to 20% by weight.

The invention will now be illustrated by the following non-limiting examples.

EXAMPLE 1

| Example # | Tested Chemical | Solubility of tested chemical in DI Water | Solubility of testes chemical in 40% AMS | Added 40% AMS wt into 10 g 0.13% tested chemical in DI water | Added 40% AMS wt into 10 g (2.5% 2,4-D + 0.13% tested chemical in DI water) |
|---|---|---|---|---|---|
| 1 | Castor oil ethoxylate-10EO | <0.007% | <0.007% | All hazy | All hazy |
| 2 | Castor oil ethoxylate-36EO | >20% | <0.036% | 0 g clear, 3.57 clear, 3.74 hazy | 0 g clear, 1.73 clear, 2.14 hazy |
| 3 | Castor oil ethoxylate-55EO | >20% | 0.036% to 0.08% | 0 g clear, 3.63 clear, 3.74 hazy | 0 g clear, 0.48 clear, 0.55 hazy |
| 4 | Cocoamine-2EO | <0.016% | <0.016% | All hazy | 0 g clear, 2.1 g clear, 2.26 g hazy |
| 5 | Cocoamine-2EO methylchloride | All clear | All clear | All clear | 0 g clear, 2.21 g clear, 2.51 g hazy |
| 6 | Hexyl glycoside | All clear | All clear | All clear | 0 g clear, 0.18 g clear, 0.36 g hazy |

In example 1, the electrolyte tolerance of 6 chemicals with and without the presence of 2,4-D amine was evaluated in ammonium sulfate system.

Examples #1, 2 and 3 show that the presence of the 2,4-D amine totally upsets the solubility trend of castor oil ethoxylate in the AMS solution. Judging from the solubility of castor oil ethoxylates in water and AMS solution, it is not possible to predict that 36EO castor oil ethoxylate would tolerate 3 times more AMS electrolyte than 55EO castor oil ethoxylate in 2.5% 2,4-D DMA solution without actually doing the experiment.

Example #4 showed that cocoamine-2EO, like # 1 castor oil ethoxylate-10EO, has little compatibility in water or AMS solution. Those skilled in the art would expect cocoamine-2EO, like castor oil ethoxylate-10EO in #1, to have poor compatibility in 2,4-D amine and AMS solution. However, cocoamine-2EO, unlike castor oil ethoxylate-10EO, has very good compatibility in 2,4-D amine and AMS solution.

Examples #5 and #6 showed that both cocoamine-2EO methylchloride and hexyl glycoside have excellent solubility in water and electrolyte tolerance (mutually soluble in 40% AMS solution). Those skilled in the art would expect both to have similar compatibility in 2,4-D amine and AMS system. However, cocoamine-2EO methylchloride is a very good compatibility agent while hexyl glycoside, which is a well known compatibility agent for other applications, is a poor compatibility agent in 2,4-D amine and AMS system.

EXAMPLE 2

In this example, the appearance of a 10 g solution of (2.5 wt % ai 2,4-D DMA+tested chemical) was evaluated after adding 40% AMS

| | | | | Addition Weight of (grams) 40% AMS | |
|---|---|---|---|---|---|
| Tested Chemical | Trade Name of tested chemical | wt % a.i. of tested chemical | 0 gram Appearance | System was clear after adding | System was cloud after adding |
| None (i.e., 2.5% 2,4-D DMA) | None | 0.00% | Clear | 0.217 | 0.267 |
| Nonylphenol-4EO | Ethylan NP-40 | 0.13% | cloudy | cloudy | 0 |
| PO-EO-PO block copolymer (MW 3600 40% EO) | Pluronic 25 R4 | 0.13% | cloudy | cloudy | 0 |
| Trideceth-4 | Ethylan TD-40 | 0.13% | cloudy | cloudy | 0 |
| Castor oil ethoxylate (10EO) | Emulpon CO-100 | 0.13% | Haze | Haze | 0 |
| Nonylphenol-6EO (5EO) | Ethylan NP-60 | 0.13% | Hazy | Hazy | 0 |
| Castor oil ethoxylate | Emulpon CO-50 | 0.13% | very cloudy | very cloudy | 0 |
| Sodium dioctyl sulfonsuccinate | Lankropol 4500 | 0.13% | very cloudy | very cloudy | 0 |
| Tall oil fatty acid-4EO | Witconol FA-40 | 0.13% | very cloudy | very cloudy | 0 |
| EO-PO-EO Block copolymer (10% EO) MW 1100 | Pluronic L31 | 0.13% | Haze | | 0.056 |
| Cocoamine-2EO oxide | Aromox C/12 | 0.13% | Clear | | 0.096 |
| Sodium lauryl sulfate | Witcolate WAC-LA | 0.04% | Clear | | 0.101 |
| Ethoxylated (6EO) caprylic & capric glycerol ester | Acconon CC-6 | 0.13% | Clear | | 0.163 |
| C8-10 glycosides | Agnique PG 8166 | 0.13% | Clear | | 0.217 |
| 2-ethylhexyl glycoside | AG 6202 | 0.13% | Clear | | 0.226 |
| C9-C11 glycoside | Agnique PG 9116 | 0.13% | Clear | | 0.272 |
| Iso C13 + 4EO phosphate ester (acid) | | 0.13% | Clear | | 0.324 |
| Propyl glycosides | AG 6203 | 0.13% | Clear | | 0.329 |
| Isopropyl alcohol | IPA | 0.13% | Clear | | 0.461 |
| C8-10 + 4 EO phosphate ester (acid) | | 0.13% | Clear | | 0.488 |

| Tested Chemical | Trade Name of tested chemical | wt % a.i. of tested chemical | 0 gram Appearance | Addition Weight of (grams) 40% AMS | |
|---|---|---|---|---|---|
| | | | | System was clear after adding | System was cloud after adding |
| Alkyl ether citrate | Alkyl ether citrate (AEC-3) | 0.13% | Clear | | 0.509 |
| Sodium xylene sulfonate | Naxonate 4LS | 0.13% | Clear | | 0.524 |
| Phenol ethoxylate | Agrisol PX401 | 0.13% | Clear | | 0.577 |
| 2-propylheptanol-5 EO | Ethylan 1005 | 0.13% | Clear | | 0.633 |
| Sodium dodecylbenzene sulfonate | Witconate 90 Flake | 0.13% | Clear | 0.107 | 0.156 |
| Butyl cellosolve Acetate (C4—O—C—C—OOCC) | Dowanol DPM | 0.13% | Clear | 0.162 | 0.324 |
| Hexylglycosides | AG 6206 | 0.13% | Clear | 0.179 | 0.359 |
| 2-Ethylhexanol + 35PO + 32EO | | 0.13% | Clear | 0.246 | 0.396 |
| Na Cocoamphocarboxyglycinate | Ampholak XCO-30 | 1.25% | Clear | 0.25 | 0.508 |
| Oleylamphopolycarboxyglycinate | Ampholak XO7/C | 0.13% | Clear | 0.261 | 0.459 |
| EO-PO-EO Block copolymer (40% EO) MW 2900 | Pluronic L64 | 0.13% | clear | 0.268 | 0.31 |
| Castor oil ethoxylate-20EO | Emulpon CO 200 | 0.13% | Clear | 0.279 | 0.521 |
| Octyliminodipropionate | Ampholak YJH-40 | 1.25% | Clear | 0.283 | 0.602 |
| EO-PO-EO Block copolymer MW 3200 | Pluronic L10 | 0.13% | Clear | 0.288 | 0.328 |
| Triethyl ammonium phosphate | Phospholan TEAP | 1.25% | Clear | 0.303 | 0.535 |
| EO-PO-EO Block copolymer (30% EO) MW 1850 | Pluronic L43 | 0.13% | Clear | 0.339 | 0.402 |
| EO-PO-EO Block copolymer (50% EO) MW 1900 | Pluronic L35 | 0.13% | Clear | 0.358 | 0.44 |
| Methyl-2-pyrrolidinone | methyl-2-pyrrolidinone | 0.13% | Clear | 0.36 | 0.567 |
| EO-PO-EO Block copolymer (40% EO) MW 2200 | Pluronic L44 NF | 0.13% | Clear | 0.389 | 0.432 |
| Nonylphenol-12EO | Ethylan NP-120 | 0.13% | Clear | 0.415 | 0.502 |
| 2-propylheptanol-8EO | Ethylan 1008 | 0.13% | Clear | 0.43 | 0.526 |
| Trideceth-8 | Ethylan TD-80 | 0.13% | Clear | 0.458 | 0.684 |
| Trideceth-6 | Ethylan TD-60 | 0.13% | Clear | 0.47 | 0.717 |
| Nonylphenol-9EO | Ethylan NP-90 | 0.13% | Clear | 0.473 | 0.601 |
| Castor oil ethoxylate-55EO | Emulpon CO 550 | 0.13% | Clear | 0.476 | 0.554 |
| Soya acid ethoxylate-10EO | Soya acid + 10 EO | 0.13% | Clear | 0.482 | 0.756 |
| Nonylphenol-30EO | Ethylan NP-300 | 0.13% | Clear | 0.487 | 0.584 |
| C10-12 alcohol ethoxylate (9EO) | Ethylan SN-90 | 0.13% | Clear | 0.519 | 0.72 |
| EO-PO-EO Block copolymer (40% EO) MW 5900 | Pluronic P104 | 0.13% | Clear | 0.521 | 0.689 |
| C6-10 isopropylamine alcohol ether sulfate | Witcolate 1259 | 0.13% | Clear | 0.528 | 0.712 |
| Trideceth-10 | Ethylan TD-100 | 0.13% | Clear | 0.557 | 0.685 |
| Trideceth-12 | Ethylan TD-120 | 0.13% | Clear | 0.581 | 0.688 |
| Sodium alkylnaphthalene sulfonate, formaldehyde polymer | Morwet D-425 | 0.13% | Clear | 0.602 | 1.066 |
| C10-12 alcohol ethoxylate (12EO) | Ethylan SN-120 | 0.13% | Clear | 0.619 | 0.669 |
| Polyoxyethylene Sorbitol Tallate | Armotan AL-69-66 | 0.13% | Clear | 0.661 | 0.71 |
| Di (propylene glycol) methyl ether | | 0.13% | Clear | 0.665 | 0.829 |
| Lauryldimethyl betaine | Amphoteen 24 | 1.25% | Clear | 0.693 | 0.913 |
| Cocamide DEA | Amadol 128T | 0.13% | Clear | 0.701 | 0.987 |
| Bottom amines | Berolamine 20 | 0.13% | Clear | 0.758 | 0.839 |
| EO-PO-EO Block copolymer (70% EO) MW 12600 | Pluronic F127 | 0.13% | Clear | 0.805 | 0.849 |
| C11 alcohol ethoxylate (5EO) | | 0.13% | Clear | 0.819 | 0.918 |
| C10-12 alcohol ethoxylate (7EO) | Ethylan SN-70 | 0.13% | Clear | 0.829 | 1.033 |
| EO-PO-EO Block copolymer (70% EO) MW 6600 | Pluronic F77 | 0.13% | Clear | 0.901 | 1.022 |
| C10-12 alcohol ethoxylate (7EO) | Ethylan SN-70 | 0.13% | Clear | 0.903 | 1.026 |
| EO-PO-EO Block copolymer (80% EO) MW 13000 | Pluronic F98 | 0.13% | Clear | 0.917 | 1.014 |
| EO-PO-EO Block copolymer (80% EO) MW 8400 | Pluronic F68 | 0.13% | Clear | 0.939 | 1.13 |
| C8-10 glycosides | AG 6210 | 0.13% | Clear | 1 | 1.212 |
| C10-12 alcohol ethoxylate (5EO) | Ethylan SN-50 | 0.13% | Clear | 1.035 | 1.226 |
| Ethoxylated (20EO) sorbitol ester | Tween 20 | 0.13% | Clear | 1.037 | 1.25 |
| 2-Ethylhexanol + 13PO + 20EO | | 0.13% | Clear | 1.0719 | 1.251 |
| Tristyrylphenol + 16EO | Soprophor BSU | 0.13% | Clear | 1.084 | 2.235 |
| EO-PO-EO Block copolymer (50% EO) MW 6500 | Pluronic P105 | 0.13% | Clear | 1.251 | 1.301 |

-continued

| Tested Chemical | Trade Name of tested chemical | wt % a.i. of tested chemical | 0 gram Appearance | Addition Weight of (grams) 40% AMS | |
|---|---|---|---|---|---|
| | | | | System was clear after adding | System was cloud after adding |
| Tallowamine-14EO | Ethomeen T/24 | 0.13% | Clear | 1.273 | 1.526 |
| Tallowamine-2EO | Ethomeen T/12 | 0.13% | Clear | 1.31 | 1.513 |
| Nonylphenol-9EO carboxylate | Emcol CNP-110 | 0.13% | Clear | 1.312 | 1.692 |
| C4 with average of 52EO and 46PO | Polyoxyalkylene Glycol Butyl Ether | 0.13% | Clear | 1.325 | 1.459 |
| Cocoamine-10EO | Ethomeen C/20 | 0.13% | Clear | 1.454 | 1.541 |
| Cocoamine-5EO | Ethomeen C/15 | 0.13% | Clear | 1.478 | 1.633 |
| Tallowamine-6EO | Ethomeen T/16H | 0.13% | Clear | 1.485 | 1.751 |
| Cocodimethylamidopropylamine | Armeen APA C | 0.13% | Clear | 1.488 | 1.731 |
| Tallowamine-10EO | Ethomeen T/20 | 0.13% | Clear | 1.503 | 1.717 |
| Sodium lauryl olefin sulfonate | Witconate AOS-12 | 0.05% | Clear | 1.526 | 2.121 |
| Tall oil fatty acid amidoamine-10EO | | 0.13% | Clear | 1.591 | 2.243 |
| Castor oil ethoxylate-36EO | Emulpon CO 360 | 0.13% | Clear | 1.726 | 2.141 |
| Tallowamine-15EO methylchloride | Ethoquad T/25 | 0.13% | Clear | 1.731 | 2.014 |
| Iso C13 etheramine-5EO | | 0.13% | Clear | 1.732 | 2.045 |
| EO-PO-EO Block copolymer (50% EO) MW 4600 | Pluronic P85 | 0.13% | Clear | 1.76 | 2.018 |
| Sodium lauryl olefin sulfonate | Witconate AOS-12 | 0.13% | Clear | 1.896 | 2.546 |
| Cocotrimethyl Chloride | Arquad C33 | 0.13% | Clear | 2.038 | 2.123 |
| Tallow acid + triethanolamine + 10EO | | 0.13% | Clear | 2.087 | 3.049 |
| Cocoamine-2EO | Berol 307 | 0.13% | Clear | 2.096 | 2.264 |
| Tristyrylphenol + 15EO | TSP (EO) 14.8 Top | 0.13% | Clear | 2.102 | 2.509 |
| Cocoamine-2EO methylchloride | Ethoquad C/12 | 0.13% | Clear | 2.21 | 2.511 |
| C4 with average of 61EO and 55PO | Polyoxyalkylene Glycol Butyl Ether | 0.13% | Clear | 2.27 | 2.728 |
| Coco duoamine-3EO | Ethoduomeen CD/13 | 0.13% | Clear | 3.521 | 4.058 |

EXAMPLE 3

Figure 1:
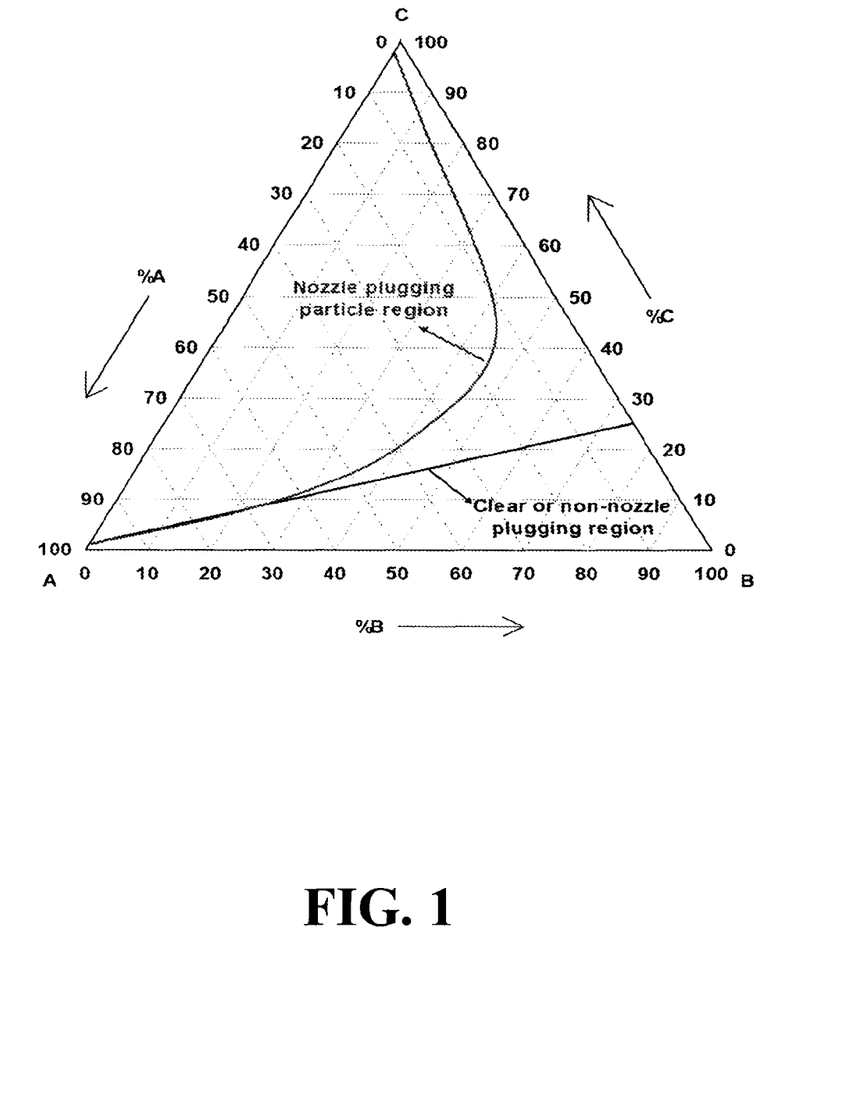
FIG. 1 is a phase diagram of 28% N fertilizer (A), Ethoquad C/12W-43.7% (B) and 2,4-D DMA (50% ai) (C).

In this example, the phase diagram of 28% N fertilizer, Ethoquad C/12, and 2,4-D DMA was constructed as shown in FIG. 1.

Figure 2:
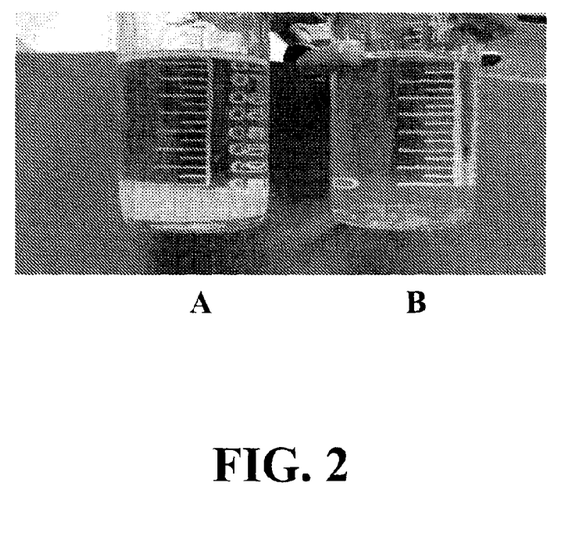
FIG. 2 is a photograph illustrating the effect of cocoamine-2EO methylchloride on coarse particle formation of 2,4-D ammonium salt. (A) 90% 28% N; 1% 2,4-D DMA; and 9% DI water. (B) 90% 28% N; 1% 2,4-D DMA; 5.5% DI water; and 3.5% Coco 2EO quat.

For example, a farmer can add 10% of a pre-mixed (8:2 Ethoquad C/12W-43.7%: 2,4-D DMA-50% ai) to 90% 28% N and obtain a non-nozzle plugging spray solution. However, if 10% pre-mixed (8:2 water: 2,4-D DMA-50% ai) is added to 90% 28% N, a hazy system with coarse particles (2,4-D NH4 salt) will form in a few minutes at room temperature. This clearly showed than cocoamine-2EO methylchloride can prevent or minimize the formation of coarse particles of the 2,4-D ammonium salt as is shown in FIG. 2.

EXAMPLE 4

Figure 3:
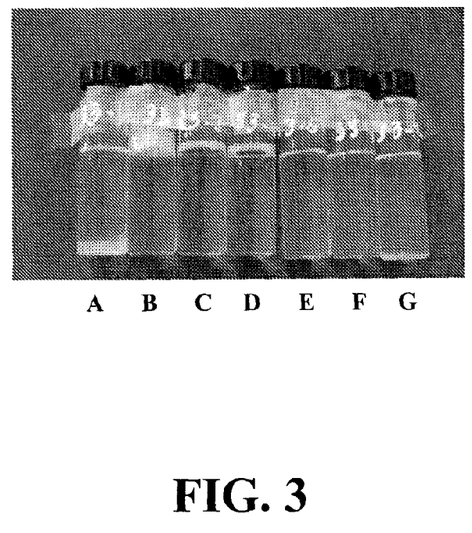
FIG. 3 is a photograph illustrating the effect of various concentrations of cocoamine-2EO ("Coco-2") and/or tallow-10EO ("Tallow-10") on crystal formation of 2,4-D. (A) 0% Coco-2/0% Tallow-10. (B) 100% Coco-2/0% Tallow-10. (C) 45% Coco-2/55% Tallow-10. (D) 50% Coco-2/50% Tallow-10. (E) 55% Coco-2/45% Tallow-10.(F) 60% Coco-2/40% Tallow-10. (G) 0% Coco-2/100% Tallow-10.

In FIG. 3, sample (0:0) was 3% 2,4-DMA (50%)+90% water (1000 ppm hardness)+7% AMS (40%) and it readily formed crystals at room temperature. Adding 0.069 g cocoamine-2EO into sample (0:0) changed it into a hazy product without crystals (sample (100:0)). Adding 0.069 g tallowamine-10EO into sample (0:0) dissolved most crystals (sample (0:100)). However, adding 0.069 g 1:1 cocoamine-2EO: tallowamine-10EO into sample (0:0) turned it into a clear solution (sample (50:50)). This demonstrated that there is a synergy between cocoamine-2EO and tallowamine-10EO in preventing 2,4-D electrolyte precipitate formation.

The first sample, (0:0), on the left had no surfactant and it had about 15% crystal at the bottom. The rest of the samples had 0.069 g surfactant post-added to the first sample. Sample (100:0) was a hazy sample with a little oily sediment at bottom. Sample (45:55) was a little hazy with some crystals at the bottom. Sample (50:50) was perfectly clear without any crystals. Sample (55:45) was a little hazy with a few crystal particles at bottom. Sample (60:40) was a little hazy with some crystal at bottom. Sample (0:100) was a little hazy with ~5% crystal at bottom.

EXAMPLE 5

System appearance after adding various chemicals into "System A" which was 100 g of 3% 2,4-D DMA (50%)+90% water (1000 ppm)+7% Ammonium sulfate (40%).

| Sample composition | Added wt, grams | Appearance | pH |
|---|---|---|---|
| System A (alone) | 0 | 10% crystals | 4.9 |
| Ethoquad C/12 43.7% | 0.815 | clear | 5.2 |
| NH4OH 28-30% | 0.079 | hazy | 8 |
| Dimethylamine 40% | 0.091 | slightly hazy | 7.8 |
| 10% NaOH | 1.07 | clear | 6 |
| 10% NaOH | 1.35 | crystals re-appeared | 10 |

It can be seen here that adding a significant amount of Ethoquad C/12 into the System A, the pH only changed slightly. However, adding inorganic base into the System A, the pH was not easy to control and it quickly changed to a high pH.

It is understood that the method also applies to in-can concentrated formulations and tank side mixed applications.

We claim:

1. A herbicidal formulation comprising (a) at least one amine salt of a phenoxy acid herbicide, (b) non-amine cations, and (c) at least one compatibility agent in an amount effective to prevent the formation of insoluble salts of said phenoxy acid herbicide, wherein said compatibility agent comprises a substance selected from the group consisting of alkoxylated quaternary surfactant, alkyl quaternary surfactant, amidoamine, alkoxylate of the reaction product of fatty acid and polyamines, ethoxylate of the reaction product of fatty acid and triethanolamine, tristyrylphenol ethoxylate, EO-PO block or random copolymer, alkyl olefin sulfonate, alkylbenzenesulfonate amine salt, castor oil alkoxylate, sodium hydroxide, potassium hydroxide, ammonium hydroxide and combinations thereof, wherein the ratio of said at least one amine salt of a phenoxy acid herbicide to said compatibility agent is from 20:1 to 1:2 by weight, and wherein said herbicidal formulation does not comprise glyphosate.

2. The formulation of claim 1 wherein said phenoxy acid herbicide is selected from the group consisting of a phenoxyacetic herbicide, phenoxybutyric herbicide, phenoxypropionic herbicide, aryloxyphenoxypropionic herbicide, 4-CPA, 2,4-D, 3,4-DA, MCPA, MCPA-thioethyl, 4-CPB, 2,4-DB, 3,4-DB, MCPB, cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and combinations thereof.

3. The formulation of claim 1 wherein said compatibility agent is i. an alkoxylated quaternary surfactant of the formula:

wherein R1 is a straight or branched chain, saturated or unsaturated alkyl group having from 8 to 22 carbon atoms; R2 is a straight or branched chain, saturated or unsaturated alkyl group having from 1 to 4 carbon atoms; and A is $C_iH_{2i}$ where i is 2 to 4; B is $C_jH_{2j}$ where j is 2 to 6; and $X^-$ is a compatible anion, f is zero to 10; m and n is an integer of from 1-30 with the proviso that m+n is at least 2, p is 1 to 7 and g is any number from zero to 6 for each p and independent of p, and q is 1 to 7 with a proviso that p is greater than q;

ii. an alkyl quaternary surfactant of the formula wherein R1 is a straight or branched chain, saturated or unsaturated alkyl group having from 8 to 22 carbon atoms; R2, R3, and R4 is independently a straight or branched chain, saturated or unsaturated alkyl group having from 1 to 4 carbon atoms; A is $C_iH_{2i}$, where i is 2 to 4; B is $C_jH_{2j}$ where j is 2 to 6; and $X^-$ is a compatible anion; f is zero to 10; p is 1 to 7 and g is any number from zero to 6 for each p and independent of p, and q is 1 to 7 with a provision that p is greater than q;

iii. an amidoamine of the formula:

where R1 a straight or branched chain, saturated or unsaturated alkyl group having from 7 to 21 carbon atoms;

iv. Alkoxylated amido polyamines of the formula wherein R1 is a straight or branched chain, saturated or unsaturated alkyl group having from 7 to 21 carbon atoms; A is $C_iH_{2i}$, where i is 2 to 4; n, m, p, and q all is 1 to 20 independently; x and y is 0 to 5 independently with a provision of x+y greater than or equal to 1;

v. the reaction products of fatty acid and triethanolamine and its alkoxylated products of the formula wherein R1 is a straight or branched chain, saturated or unsaturated alkylene group having from 8 to 22 carbon atoms; A is $C_iH_{2i}$, where i is 2 to 4; m is 1 to 30, and n is 1 to 30;

vi. tristyrylphenol ethoxylate with 8-30 EO and its phosphate or salts thereof;

vii. EO/PO block and random copolymer of the formula, wherein R1 is H, or C4 to C10 linear or branched alkyl, A' is C2 or C3, x is 30 to 300, EO:PO >40:60 (weight ratio);

viii. alkyl olefin sulfonate having an alkyl chain length between C8 and C18 and salts thereof;

ix. castor oil EO-PO alkoxylate having a total of 25 to 50 EO+PO units;

x. Hydroxides of sodium, potassium, ammonium and mixtures thereof; or xi. mixtures thereof.

4. The formulation of claim 3 wherein said compatibility agent is selected from the group consisting of tallowamine 2-15EO methylchloride quaternary, cocoamine 2-15EO methylchloride quaternary, cocotrimethyl quaternary ammonium chloride, C13 etheramine-5EO, C8-C12 dimethylpropylamine, ethoxylate 10EO of the reaction product of tall oil and diethylenetriamine, ethoxylate 10EO of the reaction product of tallow fatty acid with triethanolamine, tristyrylphenol +13-20EO, C4 with average 52EO and 42PO, EO-PO-EO Block copolymer (50% EO) MW 4600, sodium lauryl olefin sulfonate, dodecylbenzene sulfonate isopropylamine salt, castor oil ethoxylate-36 EO, coco duoamine-3EO, and mixtures thereof.

5. The formulation of claim 3 wherein the phenoxy acid herbicide is 2,4-D.

6. The formulation of claim 5 wherein the ratio of 2,4-D amine salt to the compatibility agent is from 10:1 to 1:1.5 by weight.

7. The formulation of claim 5 wherein the ratio of 2,4-D amine salt to the compatibility agent is from 5:1 to 1:1 by weight.

8. The formulation of claim 5 wherein the concentration of 2,4-D amine salt is from 0.1 to 40% by weight, based on the weight of the formulation.

9. The formulation of claim 5 wherein the concentration of 2,4-D amine salt is from 1 to 30% by weight, based on the weight of the formulation.

10. The formulation of claim 5 wherein the concentration of 2,4-D amine salt is from 2 to 20% by weight, based on the weight of the formulation.

11. A method for improving the compatibility of an amine salt of phenoxy acid herbicide with non-amine cations in a herbicidal formulation, said method comprising adding at least one compatibility agent to a herbicidal formulation comprising (a) at least one amine salt of a phenoxy acid herbicide and (b) non-amine cations, wherein the at least one compatibility agent is added to said formulation in a sufficient amount to improve the compatibility of said amine salt of said phenoxy acid herbicide with said non-amine cations,
wherein said compatibility agent comprises at least one alkoxylate quaternary surfactant, alkyl quaternary surfactant, amidoamine, alkoxylate of the reaction product of fatty acid and polyamines, ethoxylate of the reaction product of fatty acid and triethanolamine, tristyrylphenol ethoxylate, EO-PO block or random copolymer, alkyl olefin sulfonate, alkylbenzenesulfonate amine salt, castor oil ethoxylate, sodium hydroxide, potassium hydroxide, ammonium hydroxide or combinations thereof,
wherein the ratio of said at least one amine salt of a phenoxy acid herbicide to said compatibility agent is from 20:1 to 1:2 by weight, and
wherein the herbicidal formulation does not comprise glyphosate.

12. The method of claim 11 wherein said herbicide is selected from the group consisting of a phenoxy acid herbicide of phenoxyacetic herbicide, phenoxybutyric herbicide, phenoxypropionic herbicide, aryloxyphenoxypropionic herbicide, 4-CPA, 2,4-D, 3,4-DA, MCPA, MCPA-thioethyl, 4-CPB, 2,4-DB, 3,4-DB, MCPB, cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and mixtures thereof.

13. The method of claim 11 wherein said compatibility agent is
i. an alkoxylated quaternary surfactant of the formula:

wherein R1 is a straight or branched chain, saturated or unsaturated alkyl group having from 8 to 22 carbon atoms; R2 is a straight or branched chain, saturated or unsaturated alkyl group having from 1 to 4 carbon atoms; and A is $C_iH_{2i}$ where i is 2 to 4; B is $C_jH_{2j}$ where j is 2 to 6; and $X^-$ is a compatible anion, f is zero to 10; m and n is an integer of from 1-30 with the proviso that m+n is at least 2, p is 1 to 7 and g is any number from zero to 6 for each p and independent of p, and q is 1 to 7 with a proviso that p is greater than q;
ii. an alkyl quaternary surfactant of the formula wherein R1 is a straight or branched chain, saturated or unsaturated alkyl group having from 8 to 22 carbon atoms; R2, R3, and R4 is independently a straight or branched chain, saturated or unsaturated alkyl group having from 1 to 4 carbon atoms; A is $C_iH_{2i}$, where i is 2 to 4; B is $C_jH_{2j}$ where j is 2 to 6; and $X^-$ is a compatible anion; f is zero to 10; p is 1 to 7 and g is any number from zero to 6 for each p and independent of p, and q is 1 to 7 with a proviso that p is greater than q;
iii. an amidoamine of the formula:

where R1 a straight or branched chain, saturated or unsaturated alkyl group having from 7 to 21 carbon atoms;
iv. Alkoxylated amido polyamines of the formula wherein R1 is a straight or branched chain, saturated or unsaturated alkyl group having from 7 to 21 carbon atoms; A is $C_iH_{2i}$, where i is 2 to 4; n, m, p, and q all are 1 to 20 independently; x and y is 0 to 5 independently with a proviso that x+y are greater than or equal to 1;
v. the reaction products of fatty acid and triethanolamine and its alkoxylated products of the formula wherein R1 is a straight or branched chain, saturated or unsaturated alkylene group having from 8 to 22 carbon atoms; A is $C_iH_{2i}$ where i is 2 to 4; m is 1 to 30, and n is 1 to 30;
vi. tristyrylphenol ethoxylate with 8 - 30 moles ethoxylation and its phosphate or salts thereof;
vii. EO/PO block and/or random copolymer of the formula, wherein R1 is H, or C4 to C10 linear or branched alkyl, A' is C2 or C3, x is 30 to 300, EO:PO>40:60 (weight ratio);

viii. alkyl olefin sulfonate having an alkyl chain length between C8 and C18 and salts thereof;

ix. castor oil EO-PO alkoxylate having a total of 25 to 50 EO+PO units;

x. Hydroxides of sodium, potassium, ammonium and mixtures thereof; or xi. mixtures thereof.

14. The method of claim 11 wherein said compatibility agent is selected from the group consisting of tallowamine 2-15EO methyl chloride quaternary, cocoamine 2-15 EO methylchloride quaternary, coco trimethly quaternary ammonium chloride, C13 etheramine-5EO, C8-C12 dimethylpropylamine, ethoxylate 10EO of the reaction product of tallow fatty acid with triethanolamine, tristyrylphenol +13-20EO, C4 with average of 52EO and 46PO, EO-PO-EO Block copolymer (50% EO) MW 4600, sodium lauryl olefin sulphonate, dodecylbenzene sulfonate isopropylamine salt, castor oil ethoxylate 36EO, coco duoamine-3EO, and mixtures thereof.

15. The method of claim 11 wherein the phenoxy acid herbicide is 2,4-D.

16. The method of claim 15 wherein the ratio of 2,4-D amine salt to the compatibility agent is from 10:1 to 1:1.5 by weight, based on the weight of the formulation.

17. The method of claim 15 wherein the concentration of 2,4-D amine salt is from 0.1 to 40% by weight, based on the weight of the formulation.

18. The formulation of claim 3 wherein in formula i), A is $C_2H_4$, f=0, g=0, m+n is 2 to 20, R2 is methyl group, p=1, and X is chloride.

19. The formulation of claim 3 wherein in formula ii) A is $C_2H_4$, f=0, g=0, R2 is methyl group, R3 is a methyl group, R4 is a methyl group, p=1, and X is chloride.

20. The formulation of claim 3 wherein in formula iv), R1 is derived from tall oil, coconut oil, soya oil, corn, and/or tallow.

21. The formulation of claim 3 wherein $X^-$ is a compatible i anion selected from the group consisting of methyl sulfate and chloride.

22. The formulation of claim 13 wherein $X^-$ is a compatible i anion selected from the group consisting of methyl sulfate and chloride.

23. The formulation of claim 1 wherein the non-amine cations are selected from the group consisting of ammonium, potassium, sodium, calcium, magnesium cations, and combination thereof.

24. The method of claim 11 wherein the non-amine cations are selected from the group consisting of ammonium, potassium, sodium, calcium, magnesium cations, and combination thereof.

25. A herbicidal formulation comprising (a) at least one amine salt of a phenoxy acid herbicide, (b) non-amine cations, and (c) at least one compatibility agent in an amount effective to prevent the formation of insoluble salts of said phenoxy acid herbicide, wherein the ratio of said at least one amine salt of a phenoxy acid herbicide to said compatibility agent is from 20:1 to 1:2 by weight, with the proviso that the herbicidal formulation does not comprise phosphate esters or glyphosate.

26. The formulation of claim 25 wherein said phenoxy acid herbicide is selected from the group consisting of a phenoxyacetic herbicide, phenoxybutyric herbicide, phenoxypropionic herbicide, aryloxyphenoxypropionic herbicide, 4-CPA, 2,4-D, 3,4-DA, MCPA, MCPA-thioethyl, 4-CPB, 2,4-DB, 3,4-DB, MCPB, cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and combinations thereof.

27. The formulation of claim 25 wherein said compatibility agent comprises a substance selected from the group consisting of alkoxylated quaternary surfactant, alkyl quaternary surfactant, alkoxylated amine, amidoamine, alkoxylate of the reaction product of fatty acid and polyamines, ethoxylate of the reaction product of fatty acid and triethanolamine, tristyrylphenol ethoxylate, EO-PO block or random copolymer, alkyl olefin sulfonate, alkylbenzenesulfonate amine salt, castor oil alkoxylate, sodium hydroxide, potassium hydroxide, ammonium hydroxide and combinations thereof.

28. The formulation of claim 27 wherein said compatibility agent is i. an alkoxylated quaternary surfactant of the formula:

wherein R1 is a straight or branched chain, saturated or unsaturated alkyl group having from 8 to 22 carbon atoms; R2 is a straight or branched chain, saturated or unsaturated alkyl group having from 1 to 4 carbon atoms; and A is $C_iH_{2i}$ where i is 2 to 4; B is $C_jH_{2j}$ where j is 2 to 6; and $X^-$ is a compatible anion, f is zero to 10; m and n is an integer of from 1-30 with the proviso that m+n is at least 2, p is 1 to 7 and g is any number from zero to 6 for each p and independent of p, and q is 1 to 7 with a proviso that p is greater than q;

ii. an alkyl quaternary surfactant of the formula wherein R1 is a straight or branched chain, saturated or unsaturated alkyl group having from 8 to 22 carbon atoms; R2, R3, and R4 is independently a straight or branched chain, saturated or unsaturated alkyl group having from 1 to 4 carbon atoms; A is $C_iH_{2i}$ where i is 2 to 4; B is $C_jH_{2j}$ where j is 2 to 6; and $X^-$ is a compatible anion; f is zero to 10; p is 1 to 7 and g is any number from zero to 6 for each p and independent of p, and q is 1 to 7 with a provision that p is greater than q;

iii. an alkoxylated amine of the formula wherein R1 is a straight or branched chain, saturated or unsaturated alkyl group having from 8 to 22 carbon atoms; A is $C_iH_{2i}$, where i is 2 to 4; and B is $C_jH_{2j}$ where j is 2 to 6; f is zero to 10; m and n is an integer of from 0-30 with the proviso that m+n is at least 1, p is 1 to 7 and g is any number from zero to 6 for each p and independent of p;

iv. an amidoamine of the formula :

where R1 a straight or branched chain, saturated or unsaturated alkyl group having from 7 to 21 carbon atoms;
v. Alkoxylated amido polyamines of the formula wherein R1 is a straight or branched chain, saturated or unsaturated alkyl group having from 7 to 21 carbon atoms; A is $C_iH_{2i}$, where i is 2 to 4; n, m, p, and q all is 1 to 20 independently; x and y is 0 to 5 independently with a provision of x+y greater than or equal to 1;
vi. the reaction products of fatty acid and triethanolamine and its alkoxylated products of the formula wherein R1 is a straight or branched chain, saturated or unsaturated alkylene group having from 8 to 22 carbon atoms; A is $C_iH_{2i}$ where i is 2 to 4; m is 1 to 30, and n is 1 to 30;
vii. tristyrylphenol ethoxylate with 8 -30 EO and its phosphate or salts thereof;
viii. EO/PO block and random copolymer of the formula, wherein R1 is H, or C4 to C10 linear or branched alkyl, A' is C2 or C3, x is 30 to 300, EO:PO>40:60 (weight ratio);
ix. alkyl olefin sulfonate having an alkyl chain length between C8 and C18 and salts thereof;
x. castor oil EO-PO alkoxylate having a total of 25 to 50 EO+PO units;
xi. Hydroxides of sodium, potassium, ammonium and mixtures thereof; or
xii. mixtures thereof.

29. The formulation of claim 28 wherein said compatibility agent is selected from the group consisting of tallowamine 2-15EO methylchloride quaternary, cocoamine 2-15EO methylchloride quaternary, cocotrimethyl quaternary ammonium chloride, cocoamine ethoxylate 2-20EO, tallowamine ethoxylate 2-20EO, C13 etheramine-5EO, C8-C12 dimethylpropylamine, ethoxylate 10EO of the reaction product of tall oil and diethylenetriamine, ethoxylate 10EO of the reaction product of tallow fatty acid with triethanolamine, tristyrylphenol +13-20EO, C4 with average 52EO and 42PO, EO-PO-EO Block copolymer (50% EO) MW 4600, sodium lauryl olefin sulfonate, dodecylbenzene sulfonate isopropylamine salt, castor oil ethoxylate-36 EO, coco duoamine-3EO, and mixtures thereof.

30. A method for improving the compatibility of an amine salt of phenoxy acid herbicide with non-amine cations in a herbicidal formulation, said method comprising adding at least one compatibility agent to a herbicidal formulation comprising (a) at least one amine salt of a phenoxy acid herbicide and (b) non-amine cations, wherein the at least one compatibility agent is added to said formulation in a sufficient amount to improve the compatibility of said amine salt of said phenoxy acid herbicide with said non-amine cations, wherein the ratio of said at least one amine salt of a phenoxy acid herbicide to said compatibility agent is from 20:1 to 1:2 by weight, with the proviso that the compatibility agent does not comprise phosphate esters or glyphosate.

31. The method of claim 30 wherein said herbicide is selected from the group consisting of a phenoxy acid herbicide of phenoxyacetic herbicide, phenoxybutyric herbicide, phenoxypropionic herbicide, aryloxyphenoxypropionic herbicide, 4-CPA, 2,4-D, 3,4-DA, MCPA, MCPA-thioethyl, 4-CPB, 2,4-DB, 3,4-DB, MCPB, cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and mixtures thereof.

32. The method of claim 30 wherein said compatibility agent comprises at least one alkoxylate quaternary surfactant, alkyl quaternary surfactant, alkoxylated amine, amidoamine, alkoxylate of the reaction product of fatty acid and polyamines, ethoxylate of the reaction product of fatty acid and triethanolamine, tristyrylphenol ethoxylate, EO-PO block or random copolymer, alkyl olefin sulfonate, alkylbenzenesulfonate amine salt, castor oil ethoxylate, sodium hydroxide, potassium hydroxide, ammonium hydroxide or combinations thereof.

33. The method of claim 32 wherein said compatibility agent is i. an alkoxylated quaternary surfactant of the formula:

wherein R1 is a straight or branched chain, saturated or unsaturated alkyl group having from 8 to 22 carbon atoms; R2 is a straight or branched chain, saturated or unsaturated alkyl group having from 1 to 4 carbon atoms; and A is $C_iH_{2i}$ where i is 2 to 4; B is $C_jH_{2j}$ where j is 2 to 6; and X⁻ is a compatible anion, f is zero to 10; m and n is an integer of from 1-30 with the proviso that m+n is at least 2, p is 1 to 7 and g is any number from zero to 6 for each p and independent of p, and q is 1 to 7 with a proviso that p is greater than q;
ii. an alkyl quaternary surfactant of the formula wherein R1 is a straight or branched chain, saturated or unsaturated alkyl group having from 8 to 22 carbon atoms; R2, R3, and R4 is independently a straight or branched chain, saturated or unsaturated alkyl group having from 1 to 4 carbon atoms; A is $C_iH_{2i}$, where i is 2 to 4; B is $C_jH_{2j}$, where j is 2 to 6; and $X^-$ is a compatible anion; f is zero to 10; p is 1 to 7 and g is any number from zero to 6 for each p and independent of p, and q is 1 to 7 with a proviso that p is greater than q;

iii. an alkoxylated amine of the formula $$R1-(OA)_f-\left[(B)_g-N\begin{array}{c}(AO)_mH\\|\\\end{array}\right]_p-(AO)_nH$$

wherein R1 is a straight or branched chain, saturated or unsaturated alkyl group having from 8 to 22 carbon atoms; A is $C_iH_{2i}$ where i is 2 to 4; and B is $C_jH_{2j}$ where j is 2 to 6; f is zero to 10; m and n is an integer of from 0-30 with the proviso that m+n is at least 1, p is 1 to 7 and g is any number from zero to 6 for each p and independent of p;

iv. an amidoamine of the formula :

$$R1-\overset{O}{\underset{\|}{C}}-\underset{H}{\overset{|}{N}}-CH_2-CH_2-CH_2-\underset{CH_3}{\overset{|}{N}}-CH_3$$

where R1 a straight or branched chain, saturated or unsaturated alkyl group having from 7 to 21 carbon atoms;

v. Alkoxylated amido polyamines of the formula $$H(OA)_m-\left[\underset{|}{\overset{(AO)_nH}{N}}-CH_2CH_2\right]_x-\underset{\underset{R1}{\overset{|}{C=O}}}{\overset{|}{N}}-\left[CH_2CH_2-\underset{|}{\overset{(AO)_pH}{N}}\right]_y-(AO)_qH$$

wherein R1 is a straight or branched chain, saturated or unsaturated alkyl group having from 7 to 21 carbon atoms; A is $C_iH_{2i}$ where i is 2 to 4; n, m, p, and q all is 1 to 20 independently; x and y is 0 to 5 independently with a provision of x+y greater than or equal to 1;

vi. the reaction products of fatty acid and triethanolamine and its alkoxylated products of the formula $$R1-\overset{O}{\underset{\|}{C}}-O-CH_2CH_2-N\begin{array}{c}(AO)_mH\\(AO)_nH\end{array}$$

wherein R1 is a straight or branched chain, saturated or unsaturated alkylene group having from 8 to 22 carbon atoms; A is $C_iH_{2i}$ where i is 2 to 4; m is 1 to 30, and n is 1 to 30;

vii. tristyrylphenol ethoxylate with 8 -30 EO and its phosphate or salts thereof;

viii. EO/PO block and random copolymer of the formula, $$R1-(OA')_rH$$

wherein R1 is H, or C4 to C10 linear or branched alkyl, A' is C2 or C3, x is 30 to 300, EO:PO>40:60 (weight ratio);

ix. alkyl olefin sulfonate having an alkyl chain length between C8 and C18 and salts thereof;

x. castor oil EO-PO alkoxylate having a total of 25 to 50 EO+PO units;

xi. Hydroxides of sodium, potassium, ammonium and mixtures thereof; or xii. mixtures thereof.

34. The method of claim 33 wherein said compatibility agent is selected from the group consisting of tallowamine 2-15EO methyl chloride quaternary, cocoamine 2-15 EO methylchloride quaternary, coco trimethly quaternary ammonium chloride cocoamine ethoxylate 2-20EO, tallowamine ethoxylate 2-20EO, C13 etheramine-5EO, C8-C12 dimethylpropylamine, ethoxylate 10EO of the reaction product of tallow fatty acid with triethanolamine, tristyrylphenol +13-20EO, C4 with average of 52EO and 46PO, EO-PO-EO Block copolymer (50% EO) MW 4600, sodium lauryl olefin sulphonate, dodecylbenzene sulfonate isopropylamine salt, castor oil ethoxylate 36EO, coco duoamine-3EO, and mixtures thereof.

35. A herbicidal formulation comprising (a) at least one amine salt of a phenoxy acid herbicide, (b) non-amine cations, and (c) at least one compatibility agent in an amount effective to prevent the formation of insoluble salts of said phenoxy acid herbicide, wherein the at least one compatibility agent is selected from the group consisting of amidoamines.

36. The formulation of claim 35 wherein said phenoxy acid herbicide is selected from the group consisting of a phenoxyacetic herbicide, phenoxybutyric herbicide, phenoxypropionic herbicide, aryloxyphenoxypropionic herbicide, 4-CPA, 2,4-D, 3,4-DA, MCPA, MCPA-thioethyl, 4-CPB, 2,4-DB, 3,4-DB, MCPB, cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and combinations thereof.

37. The formulation of claim 35 wherein the compatibility agent is iv. an amidoamine of the formula :

$$R1-\overset{O}{\underset{\|}{C}}-\underset{H}{\overset{|}{N}}-CH_2-CH_2-CH_2-\underset{CH_3}{\overset{|}{N}}-CH_3$$

where R1 a straight or branched chain, saturated or unsaturated alkyl group having from 7 to 21 carbon atoms; or v. an alkoxylated amido polyamine of the formula

$$H(OA)_m-\left[\underset{|}{\overset{(AO)_nH}{N}}-CH_2CH_2\right]_x-\underset{\underset{R1}{\overset{|}{C=O}}}{\overset{|}{N}}-\left[CH_2CH_2-\underset{|}{\overset{(AO)_pH}{N}}\right]_y-(AO)_qH$$

wherein R1 is a straight or branched chain, saturated or unsaturated alkyl group having from 7 to 21 carbon atoms; A is $C_iH_{2i}$ where i is 2 to 4; n, m, p, and q all is 1 to 20 independently; x and y is 0 to 5 independently with a provision of x+y greater than or equal to 1.

38. A method for improving the compatibility of an amine salt of phenoxy acid herbicide with non-amine cations in a herbicidal formulation, said method comprising adding at least one compatibility agent to a herbicidal formulation comprising (a) at least one amine salt of a phenoxy acid herbicide and (b) non-amine cations, wherein the at least one compatibility agent is selected from the group consisting of amidoamines, and wherein the at least one compatibility agent is added to said formulation in a sufficient amount to improve the compatibility of said amine salt of said phenoxy acid herbicide with said non-amine cations.

39. The method of claim 38 wherein said herbicide is selected from the group consisting of a phenoxy acid herbicide of phenoxyacetic herbicide, phenoxybutyric herbicide, phenoxypropionic herbicide, aryloxyphenoxypropionic herbicide, 4- CPA, 2,4-D, 3,4-DA, MCPA, MCPA-thioethyl, 4-CPB, 2,4-DB, 3,4-DB, MCPB, cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, and mixtures thereof.

40. The method of claim 38 wherein the compatibility agent is
iv. an amidoamine of the formula:

where R1 a straight or branched chain, saturated or unsaturated alkyl group having from 7 to 21 carbon atoms; or v. an alkoxylated amido polyamine of the formula wherein R1 is a straight or branched chain, saturated or unsaturated alkyl group having from 7 to 21 carbon atoms; A is $C_iH_{2i}$ where i is 2 to 4; n, m, p, and q all is 1 to 20 independently; x and y is 0 to 5 independently with a provision of x+y greater than or equal to 1.

* * * * *